United States Patent
Gaur

(10) Patent No.: US 11,441,129 B2
(45) Date of Patent: Sep. 13, 2022

(54) MODIFIED GENE SEQUENCES ENCODING CHOLINE OXIDASE AND A METHOD FOR PREPARING BETAINE USING THE SAME

(71) Applicant: ENZIBETA BIOTECH PRIVATE LIMITED, Hyderabad (IN)

(72) Inventor: Prashant Gaur, Hyderabad (IN)

( * ) Notice: Subject to any disclaimer, the term of this patent is extended or adjusted under 35 U.S.C. 154(b) by 247 days.

(21) Appl. No.: 16/651,479

(22) PCT Filed: Jul. 31, 2018

(86) PCT No.: PCT/IB2018/055712
§ 371 (c)(1),
(2) Date: May 9, 2020

(87) PCT Pub. No.: WO2019/025958
PCT Pub. Date: Feb. 7, 2019

(65) Prior Publication Data
US 2021/0355455 A1 Nov. 18, 2021

(30) Foreign Application Priority Data
Jul. 31, 2017 (IN) .............................. 201741027084

(51) Int. Cl.
*C12N 9/04* (2006.01)
*C12P 13/00* (2006.01)

(52) U.S. Cl.
CPC .......... *C12N 9/0006* (2013.01); *C12P 13/005* (2013.01); *C12Y 101/03017* (2013.01)

(58) Field of Classification Search
None
See application file for complete search history.

(56) References Cited

U.S. PATENT DOCUMENTS

| 4,245,050 | A | * | 1/1981 | Nakanishi | ............. | C12N 9/0006 |
| | | | | | | 435/840 |
| 5,079,157 | A | * | 1/1992 | Furuoya | ................ | C12N 9/0006 |
| | | | | | | 435/191 |

FOREIGN PATENT DOCUMENTS

EP 891702 A1 1/1999

OTHER PUBLICATIONS

Genbank, Accession No. X84895, 2006, ncbi.nlm.nih.gov. (Year: 2006).*
Uniprot, Accession No. Q7X2H8, 2017, www.uniprot.org. (Year: 2017).*
Ribitsch et al., Engineering of choline oxidase from Arthrobacter nicotianae for potential use as biological bleach in detergents, Appl. Microbiol. Biotechnol. 87, 2010, 1743-52. (Year: 2010).*
Finnegan et al., Structural and kinetic studies on the Ser101Ala variant of choline oxidase: Catalysis by compromise, Arch. Biochem. Biophys. 501, 2010, 207-13. (Year: 2010).*
Ghanem et al. (Spectroscopic and Kinetic Properties of Recombinant Choline Oxidase from Arthrobacter globiformis, Biochemistry 42, 2003, 15179-88. (Year: 2003).*
Sharmila P. et. al. Targeting Prokaryotic Choline Oxidase Into Chloroplasts Enhance the Potential of Photosynthetic Machinery of Plants to Withstand Oxidative Damage. Plant Physiology and Biochemistry. May 1, 2009;47(5) :391-6. (May 1, 2009) Abstract, sequence ID:AY589052.1, protein_id AAS99880.1.

* cited by examiner

*Primary Examiner* — Robert B Mondesi
*Assistant Examiner* — Todd M Epstein
(74) *Attorney, Agent, or Firm* — Rumit Ranjit Kanakia

(57) ABSTRACT

The present invention provides at least two modified gene sequences, Sequence 1 comprising of nucleotide sequence of SEQ. ID no.1, and Sequence 2 comprising of nucleotide sequence of SEQ. ID no.2, encoding the enzyme choline oxidase wherein the gene sequences have been obtained by modifying the codA gene (Accession no. X84895) encoding choline oxidase from *Arthrobacter globiformis*, and a method to enzymatically produce betaine using choline oxidases encoded by Sequence 1, and Sequence 2, wherein the enzymatically produced betaine has minimal undesired trimethylamine contamination.

9 Claims, 3 Drawing Sheets
Specification includes a Sequence Listing.

SEQUENCE LISTING

<160> NUMBER OF SEQ ID NOS: 3

<210> SEQ ID NO 1
<211> LENGTH: 1641
<212> TYPE: DNA
<213> ORGANISM: Arthrobacter globiformis

<400> SEQUENCE: 1

```
atgcacatcg acaacattga aaatctgagc gatcgcgagt ttgattatat tgtggttggt      60
ggtggtagtg ccggtgcagc agttgcagca cgtctgagcg aagatccggc agttagcgtt     120
gcactggttg aagcaggtcc ggatgatcgt ggtgttccgg aagttctgca gctggatcgt     180
tggatggaac tgctggaaag cggttatgat tgggattatc cgattgaacc gcaagaaaat     240
ggcaatagct ttatgcgtca tgcacgtgcc aaagttatgg gtggttgtag cagccataat     300
agctgtattg cattttgggc accgcgtgaa gatctggatg aatgggaagc aaaatatggt     360
gccaccggtt ggaatgcaga agcagcctgg cctctgtata aacgtctgga aaccaatgaa     420
gatgcaggtc ctgatgcacc gcatcatggt gatagcggtc cggttcatct gatgaatgtt     480
ccgcctaaag atccgaccgg tgttgcactg ctggatgcat gtgaacaggc aggtattccg     540
cgtgccaaat tcaataccgg caccaccgtt gttaatggtg caaacttttt tcagattaat     600
cgtcgtgcag atggcacccg tagcagcagc agcgttagct atattcatcc gattgttgaa     660
```

```
caagagaact ttaccctgct gaccggtctg cgtgcacgtc agctggtttt tgatgcagat      720
cgtcgttgta ccggtgtgga tattgttgat agcgcatttg gtcgtaccca tcgtctgacc      780
gcacgtaatg aagttgttct gagtaccggt gcaattgata ccccgaaact gctgatgctg      840
agcggtattg gtccggcagc acatctggca gaacatggta ttgaagttct ggttgatagc      900
cctggtgttg gtgaacatct gcaggatcat cctgaaggtg ttgttcagtt tgaagcaaaa      960
cagccgatgg ttgcagaaag cacccagtgg tgggaaattg gtattttttac cccgaccgaa     1020 gatggtctgg atcgtccgga tctgatgatg cattatggta gcgttccgtt tgatatgaat     1080
accctgcgtc atggttatcc gaccaccgaa aatggttttta gtctgacccc gaatgttacc     1140
catgcacgta gccgtggcac cgttcgtctg cgtagtcgtg attttcgtga taaaccgatg     1200
gtggatccgc gttattttac cgatccgaaa ggtcatgata tgcgtgttat ggttgcgggt     1260
attcgtaaag cacgtgaaat tgcagcacag cctgcaatgg cagaatggac cggtcgtgaa     1320
ctgagtccgg gtgttgaagc acagaccgat gaagaactgc aggattatat tcgcaaaacc     1380
cataacaccg tttatcatcc ggttggtaca gttcgtatgg gtgcagttga agatgaaatg     1440
agtccgctgg atccggaact gcgtgttaaa ggtgttacag gtctgcgcgt tgcagatgca     1500
agcgttatgc cggaacatgt taccgttaat ccgaacatta ccgtgatgat gattggtgaa     1560
cgttgtgcag atctgattcg tagcgcacgt gccggtgaaa ccaccaccgc agatgcagaa     1620
ctgagcgcag cactggcata a                                               1641

<210> SEQ ID NO 2
<211> LENGTH: 1641
<212> TYPE: DNA
<213> ORGANISM: Arthrobacter globiformis

<400> SEQUENCE: 2
atgcacctcg acaacattga taatctgatg gatcgcgagt ttgattatat tgtggttggt       60
ggtggtagtg ccggtgcagc agttgcagca cgtctgagcg aagatccggc agttagcgtt      120
gcactggttg aagcaggtcc ggatgatcgt ggtgttccgg aagttctgca gctggatcgt      180
tggatggaac tgctggaaag cggttatgat tgggattatc cgattgaacc gcaagaaaat      240
ggcaatagct ttatgcgtca tgcacgtgcc aaagttatgg gtggttgtag cagccataat      300
agctgtattg cattttgggc accgcgtgaa gatctggatg aatgggaagc aaaatatggt      360
gccaccggtt ggaatgcaga agcagcctgg cctctgtata acgtctggaa accaatgaa       420 gatgcaggtc ctgatgcacc gcatcatggt gatagcggtc cggttcatct gatgaatgtt      480
ccgcctaaag atccgaccgg tgttgcactg ctggatgcat gtgaacaggc aggtattccg      540
cgtgccaaat tcaataccgg caccaccgtt gttaatggtg caaacttttt tcagattaat      600
cgtcgtgcag atggcacccg tagcagcagc agcgttagct atattcatcc gattgttgaa      660
caagagaact ttaccctgct gaccggtctg cgtgcacgtc agctggtttt tgatgcagat      720
cgtcgttgta ccggtgtgga tattgttgat agcgcatttg gtcgtaccca tcgtctgacc      780
gcacgtaatg aagttgttct gagtaccggt gcaattgata ccccgaaact gctgatgctg      840
agcggtattg gtccggcagc acatctggca gaacatggta ttgaagttct ggttgatagc      900
cctggtgttg gtgaacatct gcaggatcat cctgaaggtg ttgttcagtt tgaagcaaaa      960
cagccgatgg ttgcagaaag cacccagtgg tgggaaattg gtattttttac cccgaccgaa    1020 gatggtctgg atcgtccgga tctgatgatg cattatggta gcgttccgtt tgatatgaat    1080
```

-continued

```
accctgcgtc atggttatcc gaccaccgaa aatggtttta gtctgacccc gaatgttacc      1140
catgcacgta gccgtggcac cgttcgtctg cgtagtcgtg attttcgtga taaaccgatg      1200
gtggatccgc gttattttac cgatccggaa ggtcatgata tgcgtgttat ggttgcgggt      1260
attcgtaaag cacgtgaaat tgcagcacag cctgcaatgg cagaatggac cggtcgtgaa      1320
ctgagtccgg gtgttgaagc acagaccgat gaagaactgc aggattatat tcgcaaaacc      1380
cataacaccg tttatcatcc ggttggtaca gttcgtatgg gtgcagttga agatgaaatg      1440
agtccgctgg atccggaact gcgtgttaaa ggtgttacag gtctgcgcgt tgcagatgca      1500
agcgttatgc cggaacatgt taccgttaat ccgaacatta ccgtgatgat gattggtgaa      1560
cgttgtgcag atctgattcg tagcgcacgt gccggtgaaa ccgccaccgc agaagcagaa      1620
ctgagcggag cactggcata a                                                1641

<210> SEQ ID NO 3
<211> LENGTH: 1641
<212> TYPE: DNA
<213> ORGANISM: Arthrobacter globiformis

<400> SEQUENCE: 3
atgcacatcg acaacatcga gaacctgagc gacagggagt tcgactacat cgtcgtcggc        60
ggcgggtccg ccggggccgc cgtcgccgcc cggctgagcg aggatcccgc agtgagcgtg       120
gcgctggtgg aggccggccc ggatgaccgc ggcgtgcccg aggtgctgca gctggaccgc       180
tggatggagc tgctggaatc gggctacgac tgggactacc cgatcgagcc gcaggagaac       240
ggcaactcct tcatgcgcca tgcccgtgcc aaggtcatgg cggctgctc cagccacaac       300
tcctgcatcg ccttctgggc cccgcgcgag gacctggacg agtgggaggc caagtacggc       360
gccaccggct ggaacgccga ggcggcctgg ccgctgtaca agcggctgga aaccaacgag       420
gacgcgggcc ggacgcgcc gcaccacggg gactccggcc ccgtgcacct gatgaacgtg       480
cccccgaagg acccgaccgg cgtcgcgctc ctggacgcct gcgagcaggc cggcatcccg       540
cgcgcgaagt caacaccgg caccaccgtg gtcaacggcg ccaacttctt ccagatcaac       600
cggcgcgcg acggcacccg ctcctccagc tcggtctcct acatccaccc gatcgtcgag       660
caggagaact tcaccctgct aaccggcctg cgcgccgcc agctggtgtt cgacgcggac       720
aggcgctgca ccggcgtcga catcgtggac tccgccttcg ccgcacccca tcggctgacg       780
gcgcgcaatg aagtcgtgct ctccaccggc gcgatcgata cgccgaagct gttgatgctc       840
tccggcatcg ccccgccgc ccacctcgcc gagcacggca tcgaggtcct ggtggactcc       900
cccggcgtgg gcgagcacct gcaggaccac ccggaaggcg tggtgcagtt cgaggccaag       960
cagcccatgt tcgccgagtc cacgcagtgg tgggagatcg gcatcttcac ccccaccgag      1020
gacggcctgg accgcccga cctgatgatg cactacggct ccgtgccgtt cgacatgaac      1080
accctgcggc acggctaccc caccacggag aacggcttca gcctcacccc gaacgtcacg      1140
cacgcccgct cccgcggcac tgtccggctg cgcagccgcg acttccgcga taagcccatg      1200
gtcgacccgc gctacttcac cgacccagag ggccatgaca tgcgcgtcat ggtcgccggc      1260
atccgcaagg cccgcgaaat cgccgcccag ccgccatgg cggaatggac cggccgcgag      1320
ctctccccccg gcgtcgaggc gcagaccgac gaggagctgc aggactacat ccgcaagacg      1380
cacaacaccg tctaccaccc cgtgggcacc gtgcgcatgg gcgcggtcga ggacgagatg      1440
tccccgctcg accccgagct gcgggtcaag ggcgtcaccg gtctgcgcgt cgccgacgcc      1500
tcggtcatgc ccgagcacgt gaccgtcaac cccaacatca ccgtcatgat gatcggcgag      1560
```

```
cgctgcgcgg accttatccg ctccgcccgc gccggtgaaa caacgacggc ggacgccgag   1620
ctgagcgcgg ccctcgccta a                                            1641
```

MODIFIED GENE SEQUENCES ENCODING CHOLINE OXIDASE AND A METHOD FOR PREPARING BETAINE USING THE SAME

FIELD OF THE INVENTION

The invention relates to novel and modified gene sequences encoding the enzyme choline oxidase and a method for enzymatically preparing betaine using the same. More specifically, the invention provides at least two modified gene sequences encoding choline oxidase, and a method for producing betaine from choline chloride using the modified choline oxidase encoded by the same.

BACKGROUND OF THE INVENTION

Betaine, also known as trimethyglycine, glycine betaine, lycine, and oxyneurine, is a neutral chemical compound and acts as a zwitterion. It has a positively charged cationic functional group such as a quaternary ammonium or phosphonium cation and a negatively charged functional group such as a carboxylate group which may not be adjacent to the cationic site.

Betaine is a modified amino acid consisting of glycine with three methyl groups that serves as a methyl donor. Biologically, it is as a methylating agent and is involved in methylation reactions and detoxification of homocysteine.

Glycine betaine, N,N,N-trimethylglycine, was first discovered in sugar beets (*Beta vugalris*), and hence named betaine. It is naturally found in many foods such as wheat, spinach, sugar beets and other plant derived products. Apart from plants it exists in microorganisms and animals as well. The physiologic function of betaine is either as an organic osmolyte to protect cells under stress or as a catabolic source of methyl groups via transmethylation for use in many biochemical pathways. In environments with limited water content and/or raised salinity, betaine can be synthesized and accumulated by certain living organisms. The mobilization of betaine from the accumulated sources involves an increase in the intracellular osmotic pressure and the capacity of the cells to retain water, making it possible for the organisms to maintain their homeostasis and thus facilitating their adaptation to the medium.

Betaine has several applications such as: an amino acid supplement in animal feed; as an osmo-protectant in farmed fish feed; as supplement in human food products such as protein powders; veterinary medicine as hepato-protectant in cattle, pigs, goats, sheep and horses;

cystadane (betaine anhydrous for oral solution) is indicated for the treatment of homo-cystinuria to decrease elevated homo-cysteine blood levels; betaine hydrochloride is used as a digestive aid, and in cosmetic compositions for protection against skin damage and ageing. Most of the animals (poultry, swine, etc.) which are grown for meat production are under considerable stress (rapid growth, high energy diets etc.); and adding supplemental betaine helps the overall health of the animal.

There are four basic routes to obtain betaine: extraction from naturally occurring compounds, chemical synthesis, fermentation and enzymatic synthesis.

1) Natural route: Betaine is naturally synthesized in beet root/beet molasses, and most of the betaine is derived from such natural sources. Betaine is a by-product along with glycerol, lactic acid, and succinic acid during fermentation of beet molasses into ethanol and stillage. Beet molasses from the sugar plants are fermented to produce ethanol. Waste stream produced after distillation is called vinasse, rich in betaine. The vinasse is passed through chromatography columns to isolate and crystallize betaine as an anhydrous salt. This and the variants of this process are the only source of natural betaine of varying grade to meet the current market demand. Natural sources of betaine are, however, limited and are variable. Frequently, climate variations seriously reduce the production of betaine from natural sources and may be insufficient to meet the prospective demands for the product.

2) Chemical route: There are several chemical routes for synthesis of betaine and the principal reactants in the process are trimethylamine and monochloroacetic acid. Betaine is synthesized chemically by reacting Trimethylamine Mono Chloroacetic acid and/or HCl to yield anhydrous or HCl salt of betaine. This is followed by a series of evaporation and purification steps. Nevertheless, the betaine produced by chemical synthesis has traces of trimethylamine in range of 2-8 g/Kg betaine which is undesirable for many applications.

This results in subdued performance of chemically synthesized betaine compared to betaine extracted from natural sources.

3) Fermentation route: U.S. Pat. No. 5,177,008 A provides a method to recover betaine, and glycerol during fermentation of natural products such as sugar beets for production of ethanol. This process involves clarification of stillage produced during the fermentation process by subjecting the stillage to a cross-flow microfiltration process utilizing inorganic membranes followed by at least two ion-exchange chromatographic process to separate glycerol and betaine. This is followed by further purification of betaine.

However, in this process betaine is only a by-product and the said process provides a good method to efficiently recover betaine from the fermentation waste. The fermentation route is still in early developmental stage, thus time to market at a competitive price is uncertain.

4) Enzymatic process: Betaine is enzymatically synthesized using the enzyme choline oxidase (EC 1.1.3.17) which catalyses the following reaction:

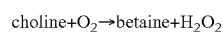

choline+$O_2$→betaine+$H_2O_2$

Choline oxidase is produced by bacteria belonging to the genus *Arthrobacter, Alkaligenes, Brevibacterium*, and *Corynebacterium*; mold fungi belonging to the genus *Aspergillus, Cylindrocarbon, Fusarium, Gibbella*, and *Penicillium*; and actinomycetes belonging to the genus *Streptomyces* and others.

Choline oxidases are oxido-reductases acting on the CHO group of the donor that participates in the metabolism of glycine, serine and threonine with oxygen as electron acceptor. The biochemical characteristics of this enzyme are isoelectric point 4.6, molecular weight about 71,000-84,000 Da, has substrate specificities for choline and betaine aldehyde, requires no coenzyme, Thermal stability below 40° C. for 10 minutes and optimum temperature of 40-45° C.

U.S. Pat. No. 4,135,980 describes the first patented choline oxidase gene isolated from *Arthrobacter* sp. which had optimum pH 8 (tris-HCl buffer); isoelectric point: 4.6; and the optimum temperature was about 40° C.

Several applications of the enzyme choline oxidase and its substrate/product betaine have been reported in prior art documents such as:

U.S. Ser. No. 09/443,087 discloses polypeptides having choline oxidase activity and nucleic acid sequences encoding the polypeptide from *Fusarium venenatum*. The invention provides method of isolation, integration into recombinant vectors, and method of expression of the polypeptides having choline oxidase activity by transforming host cells (microorganisms or plant cells) with the recombinant vectors. The invention provides improved polypeptides having choline oxidase activity over the known polypeptides for use in methods requiring choline oxidase activity such as chemiluminescent detection assays for the measurement of choline, lecithin, choline esterase activity, and phospholipase C and D activities. The invention also provides improved nucleic acids encoding the polypeptides having choline oxidase activity which may be used for enhancing cold and salt tolerance of organisms, especially plants, e.g. *Arabidopsis*.

Previously reported choline oxidases derived from *Arthrobacter* sp. showed thermostability at 40° C. at a pH around 8.0. Choline oxidase derived from Alkaligenes had molecular weight of 95,000, whose thermal stability was not higher than 37° C. Choline oxidases derived from mold and fungi showed optimal activity at around 35° C.

U.S. Pat. No. 5,187,088 describes novel thermostable choline oxidase enzymes with optimal pH range of 7.5 to 9 and optimal temperature range of about 40-55° C. These choline oxidases were derived from actinomycetes capable of producing choline oxidase and of growing at 45° C. or higher, including the genera the genera *Streptomyces, Thermoactinomyces* and *Saccharopolyspora*. This was a significant improvement over the existing choline oxidases due to the increase in thermostability of the enzyme at higher temperatures. This is a desirable feature owing to the use of the enzyme in the fields of chemical analyses and clinical tests. However, the major requirement was growing the actinomycetes sp. at temperature not less than 45° C. for producing thermostable choline oxidase. Moreover, the enzyme showed stability in a very narrow pH range i.e. pH 7.5-9.Nevertheless, there is a need to develop choline oxidase enzyme with wider stability for use in a wide range of applications. CN1185349C discloses use of gene of choline oxidase for generating transgenic temperature-tolerant plants for coping stress conditions. Gene encoding choline oxidase was integrated and expressed using recombinant DNA technology in plants such as cyanobacteria, brassicaceous plants and gramineous plants to make them temperature-tolerant. The invention also provides temperature-tolerant plants produced by said method or progenies thereof having the same properties. According to the invention, these transgenic plants obtained by inserting codA gene encoding choline oxidase derived from *Arthrobacter globiformis* showed tolerance to both of high and low temperatures.

U.S. Pat. No. 5,428,063 discloses use of betaine as a dietary supplement in pharmaceutical compositions for treating or preventing fatty infiltration, the first stage of cirrhosis of the liver comprising and administering of not less than 1500 mg of betaine per kg of body weight per day. Dietary supplementation of betaine was shown to completely protect against liver fatty infiltration in rats exposed to prolonged ethanol intake as well as carbon tetrachloride. However, for consumption by humans, it is required to use betaine which has minimal contaminants such as trimethylamine which are hazardous to health. Hence, there is a need to synthesize betaine in an economical and a safe manner EP966253 discloses use of choline oxidase in a composition for coloring or dyeing hair. The invention relates to a ready-to use composition for the oxidation dyeing of keratin fibres, and in particular of human keratin fibres such as the hair, wherein the composition comprises of a medium which is suitable for dyeing, at least one oxidation base, choline oxidase, and at least one donor for the said choline oxidase, as well as to the dyeing process using this composition. The choline oxidase used in the ready-to-use dye composition in accordance with the invention preferably represents from 0.01 to 20%, more preferably from 0.1to 5% by weight approximately relative to the total weight of the ready-to-use dye composition.

US20070042377A1 discloses use of choline oxidase in a nanoparticle based biosensor, wherein the sensor is for determining the presence of an analyte in a test sample, said sensor comprising a nanoparticulate membrane comprising nanoparticles of at least one inorganic oxide of an element selected from Group IA, IIA, IIIA,IVA, IB, IIB, IIIB, IVAB, VB, VIB,VIII3 or VIIII3 of the Periodic Table,and wherein an oxidoreductase and an electrochemical activator are diffusibly dispersed in said nanoparticulate membrane. The sensor may use other oxidoreductases other than choline oxidase such as glucose oxidase, hydrogen peroxidase, horseradish peroxidase, xanthine oxidase, cholesterol oxidase, hydrogen hydrogenase and others.

FR2877843 discloses use of product of choline oxidase, betaine, in a cosmetic or dermatological composition to prevent and/or to treat damage on the skin caused by hydric, thermal or UV induced stress and ageing of skin. More particularly, the invention refers to the use of betaine like a protective agent of the cutaneous cells subjected to a stress, in particular when it is of a hydrous nature, thermal or induced by the ultraviolet radiations (UV).The betaine used within the framework of the invention is preferably of vegetable origin, preferentially extracted from sugar beet. Betaine is obtained after purification by chromatographic separation, concentration, crystallization and drying. Preferably, the cosmetic compositions according to the invention contain from 0.01 to 10% of betaine in weight of the cosmetic composition.

US20050282261 discloses novel choline oxidases isolated from *Arthrobacter nicotianae* and *Arthrobacter aurescens*, and a hybrid choline oxidase fused from portions of the two above-stated enzymes. These choline oxidases were capable of continuously releasing hydrogen peroxide from choline and choline derivatives with the assistance of atmospheric oxygen with formation of betaine aldehyde and betaine; and exhibited an elevated specific rate of hydrogen formation. These choline oxidases were stable at in a pH range of 6-12, especially at a pH of 8-10; and at a temperature range from 10-70° C. and especially in the temperature range from 25-40° C. This provided a tremendous advantage for use in various industrial applications. The invention disclosed use of these enzymes as a bleaching agent for dye transfer inhibition and for disinfection. This included use of choline oxidase in compositions of:

a) personal healthcare products such as -body care products, shampoos, hair care products, hair dyes or bleaches, oral care, tooth care or denture care products, cosmetics;

b) detergents and cleaning agents, rinsing agents, hand washing detergents, hand dishwashing detergents, machine dishwashing detergents; and c) disinfectants and agents for bleaching or disinfectant treatment of filter media, textiles, furs, paper, skins or leather.

The invention also discloses use of these choline oxidases as a signaling reagent for the production of a light emission in a chemiluminescence assay; and use of betaine, enzymatic product of choline oxidase, in human food and animal feed as a diet supplement.

Prior art provides several uses of choline oxidase enzyme and its enzymatic product betaine in many industrial applications, dietary supplements, and cosmetic and detergent compositions. However, the major roadblock is producing choline oxidase and betaine at industrial scale.

Obtaining betaine from the natural products is not cost-effective, and therefore, the growing demand of betaine is currently met by chemically synthesized betaine whose performance is subdued. Thus, an alternate route more so using enzymatic conversion of choline using choline oxidase will lead betaine which has properties similar to the naturally obtained betaine with minimal contaminants Though several reports provide use of choline oxidase, but none advocate or demonstrate the use of choline oxidase to synthesize betaine at commercial scale.

The present invention takes into account the drawbacks of the prior art and provides novel gene sequences for encoding choline oxidase and a method to enzymatically produce betaine with properties similar to betaine extracted from natural products.

Object of the Invention

The main object of the invention is to provide a modified gene sequence, Sequence 1 comprising of nucleotide sequence of SEQ. ID no.1 encoding the enzyme choline oxidase wherein the gene sequence has been obtained by modifying the codA gene, i.e. said codA gene identified as Sequence ID No. 3 (Accession no. X84895) encoding choline oxidase from *Arthrobacter globiformis*, and a method to enzymatically produce betaine using choline oxidases encoded by Sequence 1.

Another alternative object of the invention is to provide a modified gene sequence, Sequence 2 comprising of nucleotide sequence of SEQ. ID no.2, encoding the enzyme choline oxidase wherein the gene sequences have been obtained by modifying the codA gene, i.e. said codA gene identified as Sequence ID no. 3, (Accession no. X84895) encoding choline oxidase from *Arthrobacter globiformis*, and a method to enzymatically produce betaine using choline oxidases encoded by Sequence 2.

Another object of the invention is to provide modified choline oxidases which are more thermostable at higher temperatures for longer period of time compared to native choline oxidase derived from *Arthrobacter globiformis*.

Yet another object of the invention is to provide enzymatically synthesized betaine with properties similar to betaine obtained from naturally occurring products.

Yet another object of the invention is to enzymatically produce betaine with minimal contamination of undesired trimethylamine which adversely affects the activity of betaine.

Yet another object of the invention is to provide a method for enzymatically producing betaine for industrial application using substrate choline chloride and modified gene sequences encoding choline oxidase, Sequence 1 comprising of nucleotide sequence of SEQ. ID no.1, derived by modifying the native gene sequence of codA gene, i.e. said codA gene identified as Sequence ID no. 3, (Accession no. X84895) encoding native choline oxidase from *Arthrobacter globiformis*.

Yet another object of the invention is to provide a method for enzymatically producing betaine for industrial application using substrate choline chloride and modified gene sequences Sequence 2 comprising of nucleotide sequence of SEQ. ID no.2, derived by modifying the native gene sequence of codA gene, i.e. said codA gene identified as Sequence ID no. 3, (Accession no. X84895) encoding choline oxidase from *Arthrobacter globiformis*.

Yet another object of the invention is to provide a method for producing betaine using modified choline oxidase enzymes encoded by Sequence 1 comprising of nucleotide sequence of SEQ. ID no.1, or Sequence 2 comprising of nucleotide sequence of SEQ. ID no. 2, and choline in economical manner.

Yet another object of the invention is to provide modified choline oxidases encoded by modified genes of choline oxidase which are more stable than the native choline oxidase.

Yet another object of the invention is to provide modified choline oxidases tagged with a ligand or a tag on the N' or C' terminal which are comparatively more stable at higher temperatures for longer period of time compared to similarly tagged native choline oxidase derived from *Arthrobacter globiformis*.

SUMMARY OF THE INVENTION

The present invention provides at least two modified gene sequences, Sequence 1 comprising of nucleotide sequence of SEQ. ID no.1, and Sequence 2 comprising of nucleotide sequence of SEQ. ID no.2, encoding the enzyme choline oxidase wherein the gene sequences have been obtained by modifying the codA gene, i.e. said codA gene identified as Sequence ID no. 3, (Accession no. X84895) encoding choline oxidase from *Arthrobacter globiformis*, and a method to enzymatically produce betaine using choline oxidases encoded by Sequence 1, and Sequence 2.

In the preferred embodiment the invention provides at least two modified gene sequences, Sequence 1 comprising of nucleotide sequence of SEQ. ID no.1, and Sequence 2 comprising of nucleotide sequence of SEQ. ID no.2, encoding the enzyme choline oxidase wherein the gene sequences have been obtained by modifying the codA gene, i.e. said codA gene identified as Sequence ID no. 3, (Accession no. X84895) encoding choline oxidase from *Arthrobacter globiformis*.

In an embodiment the present invention relates to at least two recombinant vectors carrying at least one modified gene Sequence 1 comprising of nucleotide sequence of SEQ. ID no.1, or Sequence 2 comprising of nucleotide sequence of SEQ. ID no.2, encoding the enzyme choline oxidase; wherein the recombinant vector comprises of a nucleic acid sequence of the present invention, a promoter, transcriptional and translational stop signals, and optionally of nucleic acid sequence encoding a tag, particularly His-tag, on either the N' or C' terminal of the encoded polypeptide sequence of choline oxidase of present invention. More specifically, the present invention relates to expression of nucleotide encoding the enzyme choline oxidase in a T7 expression system, wherein the choline oxidase polypeptide is tagged on either its N' or C' terminal with an appropriate tag molecule or ligand, more particularly His-tag, or not tagged.

In another embodiment the present invention provides two recombinant microorganisms transformed with at least one recombinant vector carrying at least one modified gene Sequence 1 comprising of nucleotide sequence of SEQ. ID no.1, or Sequence 2 comprising of nucleotide sequence of SEQ. ID no.2, encoding the enzyme choline oxidase; wherein the recombinant microorganism is preferably *Escherichia coli* but not limited thereto.

In another embodiment the invention provides a method for producing modified choline oxidase encoded by either Sequence 1 comprising of nucleotide sequence of SEQ. ID no.1, and Sequence 2 comprising of nucleotide sequence of SEQ. ID no.2, using recombinant microorganisms transformed with recombinant vectors.

In yet another embodiment the invention provides a method for producing betaine enzymatically by converting choline to betaine using the modified choline oxidases encoded by either Sequence 1 comprising of nucleotide sequence of SEQ. ID no.1, and Sequence 2 comprising of nucleotide sequence of SEQ. ID no.2.;wherein the enzyme, modified choline oxidase, is immobilized over a solid support.

The method of producing betaine from choline using the modified choline oxidase comprises the steps of:
1) making a reaction mixture comprising of:
   a) choline aqueous solution (1-50% by weight, more preferably 15-30%),and
   b) Catalase or Peroxidase 2-100 units/ml
2) carrying out a reaction using the reaction mixture in a reactor at a temperature of 20-40° C. and pH 6-9, more preferably at a temperature of from about 30-37° C. and at a pH range of 7.5-8.5; and
3) on completion of the reaction, separating the enzyme from the mixture and initiating a fresh set of reaction by contacting the recovered enzyme with a fresh reaction mixture.

BRIEF DESCRIPTION OF THE DRAWINGS

A complete understanding of the system and method of the present invention may be obtained by reference to the following drawings.

DESCRIPTION OF THE INVENTION

Figure 1:
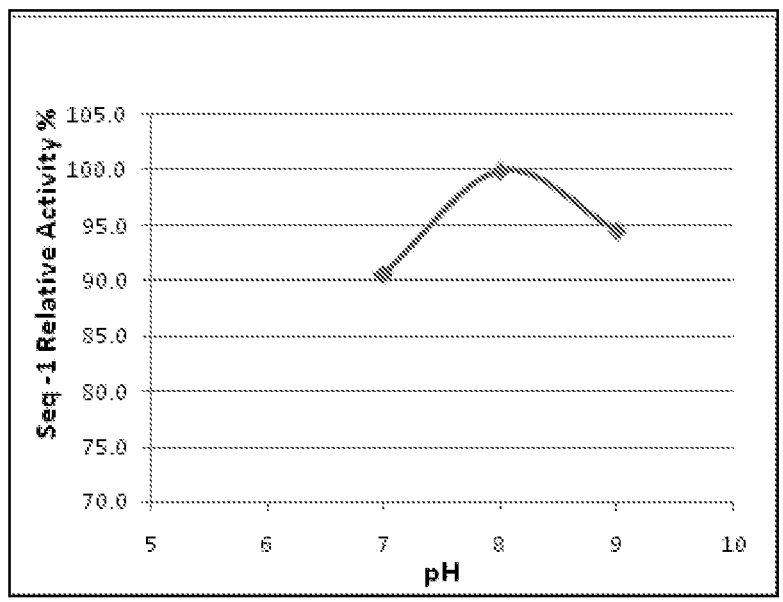
FIG. 1 depicts a graph showing the activity of modified choline oxidase encoded by Sequence 1 comprising of nucleotide sequence of SEQ. ID no. 1, at various pH conditions.

The present invention will now be described more fully hereinafter with reference to the accompanying drawings in which a preferred embodiment of the invention is shown. This invention may, however, be embodied in many different forms and should not be construed as being limited to the embodiment set forth herein. Rather, the embodiment is provided so that this disclosure will be thorough, and will fully convey the scope of the invention to those skilled in the art.

The present invention provides a modified gene sequence, Sequence 1 comprising of nucleotide sequence of SEQ. ID no.1, encoding the enzyme choline oxidase wherein the gene sequence has been obtained by modifying the codA gene, i.e. Sequence ID no. 3, (Accession no. X84895) encoding choline oxidase from *Arthrobacter globiformis*, and a method to enzymatically produce betaine using choline oxidases encoded by Sequence 1.

The present invention further provides an alternative modified gene Sequence 1 i.e. Sequence 2, comprising of nucleotide sequence of SEQ. ID no.2, encoding the enzyme choline oxidase wherein the gene sequence has been obtained by modifying the codA gene, i.e. Sequence ID no. 3, (Accession no. X84895) encoding choline oxidase from *Arthrobacter globiformis*, and a method to enzymatically produce betaine using choline oxidases encoded by Sequence 2.

In the preferred embodiment the invention provides at least two gene sequences, Sequence 1 comprising of nucleotide sequence of SEQ. ID no.1, and Sequence 2 comprising of nucleotide sequence of SEQ. ID no.2, encoding the enzyme choline oxidase wherein the gene sequences have been obtained by modifying the codA gene, i.e. Sequence ID no. 3, (Accession no. X84895) encoding choline oxidase from *Arthrobacter globiformis*.

In another embodiment of the present invention, the invention relates to at least two recombinant vectors carrying at least one modified gene Sequence 1 comprising of nucleotide sequence of SEQ. ID no.1, or Sequence 2 comprising of nucleotide sequence of SEQ. ID no.2, encoding the enzyme choline oxidase; wherein the recombinant vector comprises of a nucleic acid sequence of the present invention, a promoter, transcriptional and translational stop signals, and optionally of nucleic acid sequence encoding a tag, particularly His-tag, on either the N' or C' terminal of the encoded polypeptide sequence of choline oxidase of present invention. More specifically, the present invention relates to expression of nucleotide sequence encoding the enzyme choline oxidase derived from *Arthrobacter globiformis* in a T7 expression system, wherein the choline oxidase polypeptide is tagged on either its N' or C' terminal with an appropriate tag molecule or ligand, more particularly His-tag. The recombinant vector system can be any vector (linear or circular), a plasmid or a virus, into which the nucleotide sequence of the present invention can be inserted using recombinant DNA technology.

In yet another embodiment of the present invention, the invention relates to at least two recombinant microorganisms transformed with at least one recombinant vector carrying at least one modified gene Sequence 1 comprising of nucleotide sequence of SEQ. ID no.1, or Sequence 2 comprising of nucleotide sequence of SEQ. ID no.2, encoding the enzyme choline oxidase; wherein the recombinant microorganism is preferably *Escherichia coli* but not limited thereto.

In yet another embodiment the invention provides a method for producing modified choline oxidase encoded by either Sequence 1 comprising of nucleotide sequence of SEQ. ID no.1, or Sequence 2 comprising of nucleotide sequence of SEQ. ID no.2, using recombinant microorganisms transformed with recombinant vectors carrying at least one modified gene Sequence 1 comprising of nucleotide sequence of SEQ. ID no.1, and Sequence 2 comprising of nucleotide sequence of SEQ. ID no.2, encoding the enzyme choline oxidase. The method comprises the following steps of:
1) culturing recombinant microorganisms transformed with recombinant vectors carrying modified choline oxidase encoded by either Sequence 1 comprising of nucleotide sequence of SEQ. ID no.1, or Sequence 2 comprising of nucleotide sequence of SEQ. ID no.2, in an appropriate nutrient media either complex or synthetic for 20-48 hrs, preferably for 30 hrs, at temperature range of 20-42° C., preferably at 25° C., in a medium of pH range of 6-8.5, preferably 6.5-7.5;
2) inducing the recombinant cells to produce choline oxidase enzyme by treating them with isopropyl β-D-1-thiogalactopyranoside (IPTG) or any other inducer based on the T7 expression system carrying the modified gene encoding choline oxidase (the enzyme generally accumulates as soluble fraction and/or in inclusion bodies inside the microbes depending upon the fermentation process parameters);
3) separating the microorganisms from the nutrient media by either centrifugation or tangential flow filtration to obtain a harvest of microorganisms;
4) grinding or lysing or using digestive enzymes for breaking the harvested microorganism cells open to release the inner contents including inclusion bodies containing the enzyme, choline oxidase; and
5) isolating and purifying the enzyme choline oxidase by a combination of methods such as salting-out with ammonium sulfate, precipitation with an organic solvent such as ethanol, etc., ion-exchange chromatography, gel filtration, affinity chromatography, and the like.

In yet another embodiment the invention provides a method for producing betaine enzymatically by converting choline to betaine using the modified choline oxidases encoded by either Sequence 1 comprising of nucleotide sequence of SEQ. ID no.1, and Sequence 2 comprising of nucleotide sequence of SEQ. ID no.2.;wherein the enzyme, modified choline oxidase, is immobilized over a solid support. The choline was treated with choline oxidase using either a batch orcontinuous process. In either case, it was preferred that the enzyme, choline oxidase, be immobilized by a water-insoluble support, usually a polymer, either by physical absorption, covalent bonding, or by entrapment. In the first two methods of immobilization, a choline oxidase/water-insoluble polymer conjugate was formed which makes retention and recycling of the enzyme possible. Synthetic supports which are suitable for use with the present invention include polymers based upon acrylamide, maleic anhydride, methacrylic acid, and styrene; natural supports include agarose, cellulose, dextran and starch; and commonly used adsorbents which have been used to immobilize enzymes include affinity resins, calcium carbonate, cellulose, clays, collagen, diatomaceous earth, hydroxylapatite and the like. Another suitable method for the immobilization of the choline oxidase is by use of a hollow fiber reactor. This type of system is preferable where contamination of active chemical residues needs to be avoided, as for example in the production of food stuffs.

The method for producing betaine enzymatically by converting choline to betaine using the modified choline oxidases comprising the steps of:
1) making a reaction mixture comprising of:
   a) choline aqueous solution (1-50% by weight, more preferably 15-30% by weight) 0.1-0.5 M, more preferably 0.14 M;
   b) Catalase or Peroxidase 2-100 units/ml 2) carrying out the reaction using the reaction mixture in a reactor at a temperature of 20-40° C. and pH 6-9, more preferably at a temperature of from about 30-37° C. and at a pH of 7.5-8.5; and
3) on completion of the reaction, separating the enzyme from the mixture and initiating a fresh set of reaction by contacting the recovered enzyme with a fresh reaction mixture;

wherein,
hydrogen peroxide catalyzing agents may be added to the solution to inhibit the inactivation of the choline oxidase due to hydrogen peroxide levels to improve the efficiency of the process;
multivalent cations such as KCl or $MgCl_2$ are commonly used as thermal stabilizers and/or cofactors; and
choline to betaine conversion is 1:1 at molar level.

The present invention is more fully described hereinafter and with reference to illustrative examples. It is to be understood, however, that these examples are presented in order to more fully describe the present invention, and are correspondingly not intended to be construed to limit the present invention.

EXAMPLE 1

Synthesis and Extraction of Modified Choline Oxidase

Modified choline oxidase enzyme was synthesized using fermentation process by recombinant *Escherichia coli* transformed with recombinant vectors carrying at least one gene coding for choline oxidase, either Sequence 1 comprising of nucleotide sequence of SEQ. ID no. 1, or Sequence 2 comprising of nucleotide sequence of SEQ. ID no.2.

The medium required for the production of choline oxidase can either be synthetic or complex medium which comprises of a carbon source, nitrogen source, inorganic substance and other nutrients. Examples of carbon source include glucose, sodium gluconate, glycerol and the like; examples of nitrogen source include tryptone, peptone, casein digest, yeast extract, and the like; and examples of inorganic substance include sodium, potassium, calcium, manganese, magnesium, cobalt, and the like which are usually contained in a normal medium. Examples of preferred medium is 1% tryptone, 0.5% yeast extract, 2-3% glucose, 1.0% $K_2HPO_4$, 0.1% $NaH_2PO_4$, 0.05% $MgSO_4 \cdot 7H_2O$, 0.01% $CaCl_2 \cdot 2H_2O$ and 0.01% vitamin mixture and 0.02% trace metal mixture, in which tryptone and yeast extract is used as the sole nitrogen source, and glucose as the carbon source.

The cultivation of recombinant *E. coli* was normally done at temperature range of 20-42° C., preferably at 25° C., in a medium of pH range of 6-8.5, preferably 6.5-7.5 and the cells were cultured for 20-48 hrs, more preferably for 30 hrs. However, the culturing conditions may vary depending on various factors such as conditions of microorganism and should not be limited to those described here. Synthesis of choline oxidase is induced to the highest extent using IPTG or lactose with varied concentration for protein resulting in inclusion body form and/or as soluble fraction.

Choline oxidase got accumulated inside the recombinant cells when cultured in the above mentioned method. The resultant fermentation broth was then treated to separate the cells from the broth using centrifugation method and or tangential flow filtration employing hollow fiber or filtration cassettes. The harvested cells were either ground or lysed to extract the enzyme. The grinding of cells can be carried out in a conventional manner, for example, by means of mechanical grinding, auto-digestion with a solvent, freezing, ultrasonic treatment, pressurization, or the like. Then the enzyme was isolated and purified either by conducted by combining known methods such as salting-out with ammonium sulfate, precipitation with an organic solvent such as ethanol, etc., ion-exchange chromatography, gel filtration, affinity chromatography, and the like.

For example, bacterial cells were harvested by subjecting the resultant culture to centrifugation or tangential filtration, washed, suspended in 0.1 M Tris-HCl buffer (pH 8.0), ground with sonicator and centrifuged. The supernatant as cell—free extract was then purified using, for example, fractionation with ammonium sulfate or using affinity chromatography Ni-NTA chromatography.

Molecular weight of the modified choline oxidase encoded by either Sequence 1 comprising of nucleotide sequence of SEQ. ID no.1, or Sequence 2 comprising of nucleotide sequence of SEQ. ID no. 2., when determined by SDS-PAGE (sodium dodecyl sulfate polyacrylamide gel electrophoresis) was about 70,000 Da (70.0 kDa).

EXAMPLE 2

Enzyme Activity Assay of Modified Choline Oxidase

Choline oxidase activity was measured by two step enzymatic reaction. Choline oxidase catalyses the production of betaine, followed by production of quinoneimine through the hydrogen produced in the first enzymatic reaction.

Reaction 1 was catalyzed by choline oxidase:

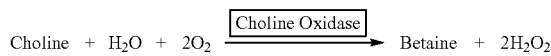

Reaction 2 was catalyzed by peroxidase:

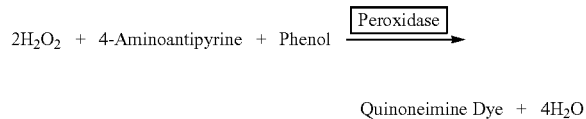

Each 100 ml of reaction mixture comprised of Tris buffer (97 mM), Choline chloride (0.14 M), EDTA (33 µM), KCl (2.2 mM), 4-Aminoantipyrine (48 mM), Phenol (2.1 mM), and Peroxidase (5 U/ml).

Enzymes were assayed by pipetting 3.0 ml of reaction mixture into a cuvette (d=1.0cm) and equilibrate at 37° C. for about 5 minutes followed by addition of 0.05 ml of the enzyme solution* and mix by gentle inversion. The increase in optical density at 500 nm against the working solution for 3 to 4 minutes in a spectrophotometer thermostated at 37° C., was recorded and the LOD per minute was calculated from the initial linear portion of the curve.

Calculation
Activity can be calculated by using the following formula:

$$\text{Volume activity (U/ml)} = \frac{\Delta OD/\min \times Vt \times df}{12.0 \times 1/2 \times 1.0 \times Vs} = \Delta OD/\min \times 10.17 \times df$$

Weight activity (U/mg)=(U/ml)×1/C

Vt: Total volume (3.05 ml)
Vs: Sample volume (0.05 ml)
12.0: Millimolar extinction coefficient of quinoneimine dye under the assay conditions (F/micromole)
½: Factor based on the fact that one mole of $H_2O_2$ produces half a mole of quinoneimine dye
1.0: Light path length (cm)
Df: Dilution factor
C: Enzyme concentration in final sample dilution (mg/ml)
Specific activity shall be defined as micromole $H_2O_2$ which is formed in 1 min by 1 mg enzyme [U/mg].

EXAMPLE 3

Determination of Optimal Ph of Choline Oxidase Activity

The optimal pH for activity of choline oxidase was determined by adding choline oxidase to a mixture of 100 mM Tris-HCl buffer, potassium phosphate buffer, water (pH 5.0 to 10.0), incubating for 10 minutes at 25° C., and measuring the activity of choline oxidase as detailed under Example 2 (37° C., pH 8.0).

Figure 2:
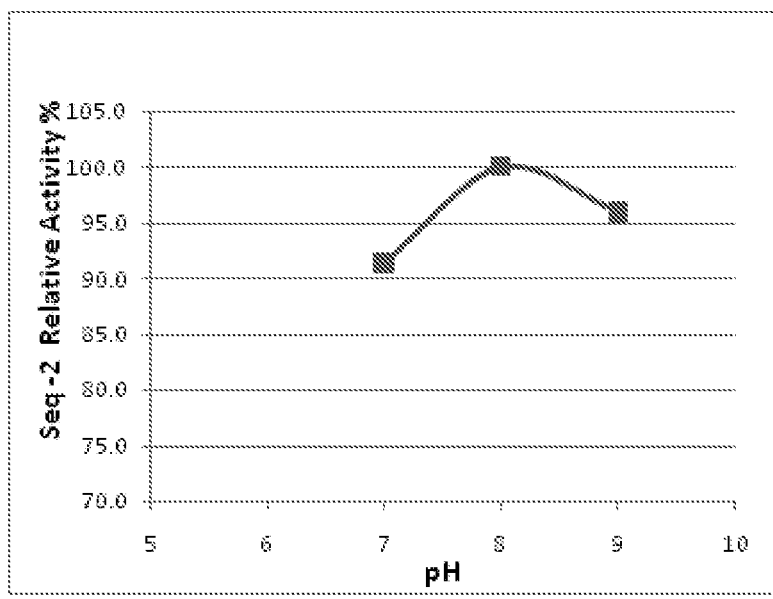
FIG. 2 depicts a graph showing the activity of modified choline oxidase encoded by Sequence 2 comprising of nucleotide sequence of SEQ. ID no. 2, at various pH conditions.

As depicted in FIG. 1 and FIG. 2, modified choline oxidases encoded by SEQ. ID no.1 and SEQ. ID no.2 are stable in the pH range of about 6.0 to 10 .0,preferably pH 7.0 to 9.0. The optimal pH is about pH 8.0.

EXAMPLE 4

Determination of Optimal Temperatue of Choline Oxidase Activity

The optimal temperature for activity of choline oxidase was determined by adding choline oxidase to a mixture of 10 mM Tris-HCl buffer (pH 8.0) at temperature ranging from 10 to 65° C., incubating the mixture under the same condition for 0-120 minutes and measuring the activity of choline oxidase as detailed under Example 2(37° C., pH 8.0).

Figure 3:
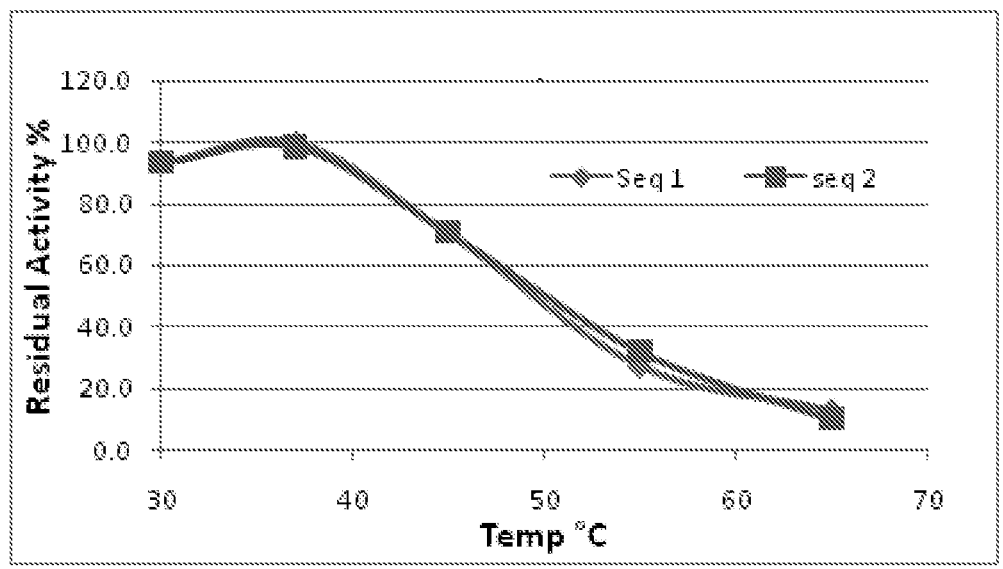
FIG. 3 depicts a graph showing the activity of modified choline oxidase encoded by Sequence 1 comprising of nucleotide sequence of SEQ. ID no. 1, and Sequence 2 comprising of nucleotide sequence of SEQ. ID no. 2, at various temperatures after incubating at the respective temperatures for 20 mins (short-term exposure to different temperatures)

Short-Term Thermal Stability
The modified choline oxidases encoded by SEQ. ID no.1 and SEQ. ID no. 2were tested for activity at various temperatures after incubating at the respective temperatures for 20 mins As depicted in FIG. 3, both the modified choline oxidases showed stability at a temperature range of 10-50° C,preferably 25-45° C., more preferably at about 37° C.

Figure 4:
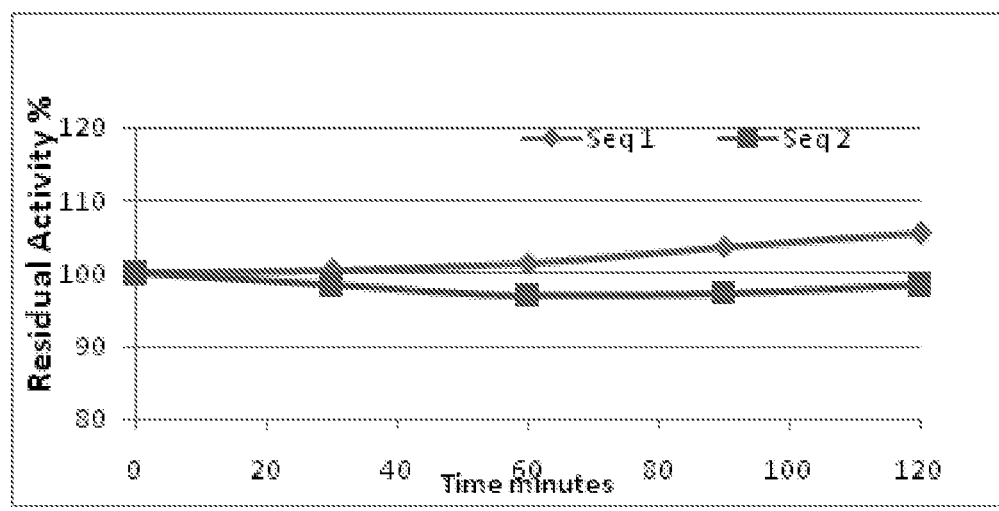
FIG. 4 depicts a graph showing the activity of modified choline oxidase encoded by Sequence 1 comprising of nucleotide sequence of SEQ. ID no.1, and Sequence 2 comprising of nucleotide sequence of SEQ. ID no. 2, at 37° C. after incubating at the respective temperatures for up to 120 mins (long-term exposure)

Long-Term Thermal Stability
The modified choline oxidases encoded by SEQ. ID no.1 and SEQ. ID no. 2 were tested for activity at 37° C. over a period of 120 mins As depicted in FIG. 4, both the modified choline oxidases enzyme reaction proceeds efficiently till up to 120 mins

EXAMPLE 5

Thermal Stability of Modified Choline Oxidase Tagged with A Ligand or A Tag

The native gene of choline oxidase derived from *Arthrobacter globiformis* and the modified gene of choline oxidase derived from *Arthrobacter globiformis*, Sequence 1 comprising of nucleotide sequence of SEQ. ID no.1, was expressed using T7 expression system encoding either the native enzyme or the modified enzyme, choline oxidase, along with a tag, more particularly His-tag. The activity of choline oxidase was determined by adding choline oxidase to a mixture of 10 mM Tris-HCl buffer (pH 8.0) at 45° C., incubating the mixture under the same condition for 0-120 minutes and measuring the activity of choline oxidase every 30 minutes as detailed under Example 2(37° C., pH 8.0).

Figure 5:
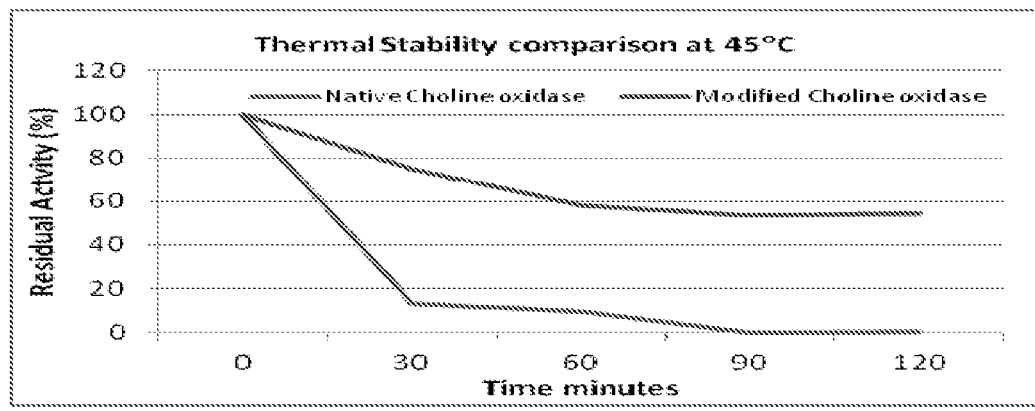
FIG. 5 depicts a graph comparing the activities of native choline oxidase derived from *Arthrobacter globiformis* and of modified choline oxidase encoded by Sequence 1 comprising of nucleotide sequence of SEQ. ID no. 1., at 45° C. when the enzymes were tagged with a ligand or a tag, more particularly His-tag.

FIG. 5 depicts a graph comparing the activities of native choline oxidase derived from *Arthrobacter globiformis* and of modified choline oxidase encoded by Sequence 1 comprising of nucleotide sequence of SEQ. ID no.1., when the enzymes were tagged with a ligand or a tag, more particularly His-tag.

The result clearly shows that His-tagged modified choline oxidase was significantly more stable than the His-tagged native choline oxidase. The modified enzyme was stable at 45° C. for more than 60 minutes, more appropriately for more than 30 minutes, whereas the His-tagged native enzyme lost around 80% of the activity within less than 30 minutes.

EXAMPLE 6

Betaine Production

The reaction mixture for the production of betaine contained:
a) 20 mM Tris-HCl buffer (pH 8), 0.129 mole of choline, 275 units of peroxidase, and 1373 units of choline oxidase in a final volume of 142 ml.
b) 20 mM Tris-HCl buffer (pH 8), 2.486 mole of choline, 6300 units of peroxidase, and 31012 units of choline oxidase in a final volume of 150 ml.

The reaction was carried at 37° C. and samples were withdrawn intermittently to analyse the conversion of choline to betaine. The enzymes source was purified choline oxidase either from Seq1 or the Seq 2, described above.

Figure 6:
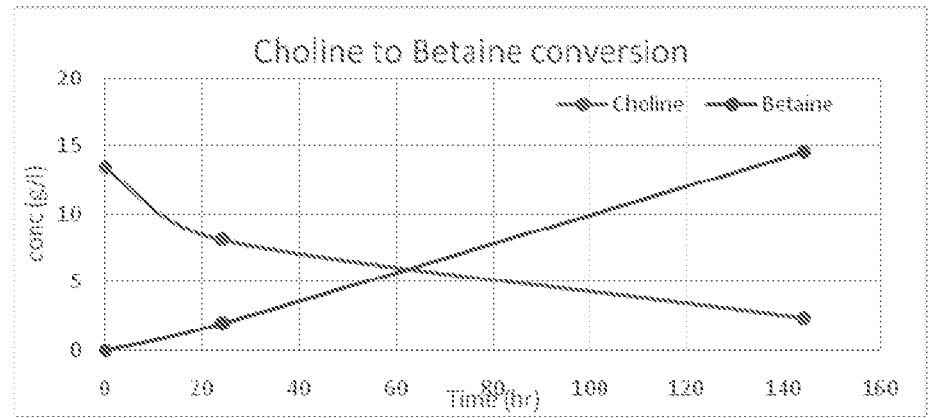
FIG. 6 depicts a graphical representation of conversion ratio of choline to betaine using modified choline oxidase encoded by Sequence 1 comprising of nucleotide sequence of SEQ. ID no.1, or Sequence 2 comprising of nucleotide sequence of SEQ. ID no.2.

The amount of betaine formed was determined by the liquid chromatography-mass spectrometry (LC-MS). Similarly, the reactions were setup with varied concentration of substrate and enzyme and conversion were estimated using LC-MS. As depicted in FIG. 6, choline is converted to betaine with high efficiency.

TABLE 1

Estimation of the reaction products of choline oxidation with choline oxidase either Seq ID 1 or Seq ID 2

| Compound | Amount (Mole) |
|---|---|
| A | |
| Choline added | 0.129 |
| Betaine formed | 0.124 |
| B | |
| Choline added | 2.486 |
| Betaine formed | 2.467 |

Tri-Methyl Amine estimated in enzyme reactor:
During the above enzyme reactor setup for choline to betaine conversion the TMA was also estimated using LCMS method.

TABLE 2

Provides estimated trimethylamine (TMA) in the reaction

| Compound | Amount (Mole) |
|---|---|
| TMA - (enzyme reactor – initial sample) | 0.010 |
| TMA - (enzyme reactor – termination sample) | 0.000 |

As it is evident from Table 2, the presence of TMA is minimal and hence betaine produced is of high quality.

I claim:

1. A choline oxidase polypeptide comprising an amino acid sequence encoded by the nucleotide sequence of SEQ ID NO: 2, wherein the choline oxidase polypeptide is tagged with a histidine tag on an N- or C-terminus of the choline oxidase polypeptide.

2. A modified gene sequence of codA gene comprising the nucleotide sequence of SEQ ID NO: 2 for encoding choline oxidase;
wherein
the choline oxidase encoded by said nucleotide sequence has stability in the pH range 7.0 to 9.0;
the choline oxidase encoded by said nucleotide sequence has stability at a temperature range of 10-50 °C.;
the choline oxidase encoded by said nucleotide sequence has stability at a temperature range of 10-50 °C. for up to 120 minutes; and
the choline oxidase thus encoded is useful to produce betaine from choline.

3. A method for producing betaine from choline comprising the steps of: a) making a reaction mixture comprising of choline aqueous solution, an enzyme and optionally a hydrogen peroxide catalyzing agent;
b) carrying out a reaction using the reaction mixture in a reactor; and
c) on completion of the reaction, separating the enzyme from the mixture;
wherein the enzyme comprises choline oxidase encoded by the nucleotide sequence of SEQ ID NO: 2; and
the method has choline to betaine conversion efficiency of 1:1 molar ratio.

4. The method as claimed in claim 3, wherein the choline aqueous solution is 1-50% by weight.

5. The method as claimed in claim 3, where the choline aqueous solution is 15-30% by weight.

6. The method as claimed in claim 3, wherein the hydrogen peroxide catalyzing agent is Peroxidase.

7. The method as claimed in claim 3, wherein, the reaction of step b) is carried at a temperature range of 20-40° C. and a pH range of 6-9.

8. The method as claimed in claim 3, wherein, the reaction is carried in the presence of thermal stabilizers and/or cofactors.

9. The method as claimed in claim 8, wherein, the thermal stabilizers comprise KCl.

\* \* \* \* \*